US012735673B2

(12) United States Patent
Mao et al.

(10) Patent No.: US 12,735,673 B2
(45) Date of Patent: *Sep. 15, 2026

(54) ***SACCHAROPOLYSPORA* AND APPLICATION THEREOF IN REDUCING BIOGENIC AMINES**

(71) Applicants: Jiangnan University, Wuxi (CN); Jiangnan University (Shaoxing) Industrial Technology Research Institute, Shaoxing (CN)

(72) Inventors: Jian Mao, Wuxi (CN); Shuangping Liu, Wuxi (CN); Zhilei Zhou, Wuxi (CN); Zhongwei Ji, Wuxi (CN); Xiao Han, Shaoxing (CN); Jing Zhang, Wuxi (CN)

(73) Assignees: Jiangnan University, Wuxi (CN); Jiangnan University (Shaoxing) Industrial Technology Research Institute, Shaoxing (CN)

( * ) Notice: Subject to any disclaimer, the term of this patent is extended or adjusted under 35 U.S.C. 154(b) by 767 days.

This patent is subject to a terminal disclaimer.

(21) Appl. No.: 18/050,085

(22) Filed: Oct. 27, 2022

(65) Prior Publication Data

US 2023/0193195 A1 Jun. 22, 2023

Related U.S. Application Data

(63) Continuation of application No. PCT/CN2021/077378, filed on Feb. 23, 2021.

(30) Foreign Application Priority Data

Aug. 13, 2020 (CN) ......................... 202010811653.3

(51) Int. Cl.

*C12N 1/20* (2026.01)
*A23L 33/135* (2016.01)

(Continued)

(52) U.S. Cl.

CPC ............ *C12N 1/205* (2021.05); *A23L 33/135* (2016.08); *A23L 33/20* (2016.08); *A24B 15/307* (2013.01)

(58) Field of Classification Search

None

See application file for complete search history.

(56) References Cited

U.S. PATENT DOCUMENTS 12,089,619 B2 * 9/2024 Mao ........................... C12J 1/04

FOREIGN PATENT DOCUMENTS

| CN | 111961615 A | 11/2020 |
|---|---|---|
| CN | 111979146 A | 11/2020 |
| CN | 111979148 A | 11/2020 |

OTHER PUBLICATIONS

Gastronomixs, Einkorn wheat koji, retereived from the web gastronomixs.com/en/components/6175-einkorn-wheat-koji, 2025 (Year: 2025).*

Venkat, Pure Glycerin_ Benefits, Uses, and Where to Get It, retrieved from www.webmd.com/beauty/what-is-pure-glycerin (Year: 2025).*

Milky Day blog, How to make low fat milk, 2025, milkyday.com/blog/2018/09/15/how-to-make-low-fat-milk/ (Year: 2025).*

(Continued)

*Primary Examiner* — Thane Underdahl
*Assistant Examiner* — Mary A Crum
(74) *Attorney, Agent, or Firm* — IPro, PLLC; Na Xu

(57) ABSTRACT

The present disclosure discloses *Saccharopolyspora* and application thereof in reducing biogenic amines, belonging to the technical field of food fermentation. *Saccharopolyspora jiangxiensis* J3 is screened from wheat koji and has been preserved in China Center for Type Culture Collection (CCTCC) on Apr. 30, 2020, with a preservation number of CCTCC NO: M 2020104. According to the present disclosure, the strain is applied to a food fermentation system, and (Continued)

results show that the strain does not affect normal fermentation of food, and has an effect of reducing the content of biogenic amines in fermented alcoholic drinks, fermented food and fermented condiments, so that the strain has broad application prospects in the field of food brewing.

5 Claims, 4 Drawing Sheets

Specification includes a Sequence Listing.

(51) Int. Cl.

| | |
|---|---|
| ***A23L 33/20*** | (2016.01) |
| ***A24B 15/30*** | (2006.01) |
| ***C12N 1/205*** | (2026.01) |

(56) References Cited

OTHER PUBLICATIONS

Aidoo, Roger Philip, et al. "Industrial manufacture of sugar-free chocolates-Applicability of alternative sweeteners and carbohydrate polymers as raw materials in product development." Trends in Food Science & Technology 32.2 (2013): 84-96. (Year: 2013).*

Gutiérrez, María C., et al. "Bacteria incorporation in deep-eutectic solvents through freeze-drying." Angew. Chem 49 (2010): 2158-2162. (Year: 2010).*

Maicas, Sergi. "Yeast Fermentation and the Make of Biotechnological Products." Microorganisms 11.6 (2023): 1463. (Year: 2023).*

Jianli Zhang et. al., "*Saccharopolyspora jiangxiensis* sp nov. isolated from grass-field soil", International Journal of Systematic and Evolutionary Microbiology,vol. 59,May 31, 2009.p. 1076-1081.

* cited by examiner

```
                         SEQUENCE LISTING


Sequence total quantity: 3
SEQ ID NO: 1           moltype = DNA  length = 1370
FEATURE                Location/Qualifiers
source                 1..1370
                       mol_type = genomic DNA
                       organism = Saccharopolyspora jiangxiensis
SEQUENCE: 1
gggttgggcc atgggcttcg ggtgttaccg actttcatga cgtgacgggc ggtgtgtaca  60
aggcccggga acgtattcac cgcagcaatg ctgatctgcg attactagcg actccgactt  120
cacggggtcg agttgcagac cccgatccga actgagaccg gctttaaggg attcgctcaa  180
cctcacgatc tcgcagccct ctgtaccggc cattgtagca tgtgtgaagc cctgggcata  240
aggggcatga tgacttgacg tcatccccac cttcctccga gttgaccccg gcagtccccc  300
acgagtcccc ggcatcaccc gctggcaaca tagggcaagg gttgcgctcg ttgcgggact  360
taacccaaca tctcacgacc acgaagctga cgacagccat gcacctacct gtacaccaac  420
cacaaaggga aaccccctct caggggctgt ctagtgcatg tcaaaccmag gtaaggttyt  480
tcgcgttgca tsgaattaat ccacatgctc cgccgcttgt gcgggccccc gtcaattcct  540
ttgagtttta gccttgcggc cgtactcccc aggcggggcg cttaatgcgt ttagctacgg  600
cacggaaaca gtggaaccca tccccacacc tagcgcccaa cgtttacggc gtggactacc  660
agggtatcta atcctgttcg ctccccacgc tttcgctcct cagcgtcagt atcggcccag  720
agacccgcct tcgccaccgg tgttcctcct gatatctgcg catttcaccg ctacaccagg  780
aattccagtc tcccctaccg aactcaagtc tgcccgtatc caccgcaagc caggagttaa  840
gctcccggtt ttcacgatag acgcgacaaa ccgcctacga gctctttacg cccaataaat  900
ccggacaacg ctcgcaccct acgtattacc gcggctgctg gcacgtagtt tagccggtgc  960
tttcttctac accttactcg tcaacccyaa aggggccttc gtcgatgtcg aaagtaggtt  1020
tacaacccga aggccgtcat cccccacgcg gcgttgctgc gtcaggcttt cgcccattgc  1080
gcaagattcc ccactgctgc ctcccgtagg agtctgggcc gtgtctcagt cccagtgtgg  1140
ccggtcaccc tctcaggccg gctacccgtc gtcgccttgg taggccatca ccccaccaac  1200
aagctgatag gccgcgggct catcctgcac cgccggaact ttccacacac gaagatgcct  1260
ccatgtgtcc tatccggtat tagaccccgt ttccaaggct tatcccagag tgcagggcag  1320
attacccacg tgttactcac ccgttcgcca ctcatccaca cccgaaagtg             1370

SEQ ID NO: 2           moltype = DNA  length = 20
FEATURE                Location/Qualifiers
source                 1..20
                       mol_type = other DNA
                       organism = synthetic construct
SEQUENCE: 2
agagtttgat cctggctcag                                              20

SEQ ID NO: 3           moltype = DNA  length = 19
FEATURE                Location/Qualifiers
source                 1..19
                       mol_type = other DNA
                       organism = synthetic construct
SEQUENCE: 3
ggttaccttg ttacgactt                                               19
```

*SACCHAROPOLYSPORA* AND APPLICATION THEREOF IN REDUCING BIOGENIC AMINES

REFERENCE TO SEQUENCE LISTING

The instant application contains a Sequence Listing in XML format as a file named "YGHY-2022-37-SEQ.xml", created on Aug. 26, 2022, of 5179 bytes in size, and which is hereby incorporated by reference in its entirety.

TECHNICAL FIELD

The present disclosure relates to *Saccharopolyspora* and application thereof in reducing biogenic amines, belonging to the technical field of food fermentation.

BACKGROUND

Huangjiu is a kind of brewed wine, which is generally prepared by using glutinous rice, corn and millet as raw materials, and adding wheat koji and yeast as a saccharifying agent and a starter; and it is obtained by cooking, adding koji, carrying out saccharification and fermentation, pressing, filtering, decocting, storing and blending. In addition to the main components such as water and ethanol, the huangjiu also contains 18 kinds of amino acids, including 8 essential amino acids, the 8 essential amino acids are many times more than those in the same amount of wine and beer, so that the regular drinking of huangjiu is beneficial to health; the huangjiu is rich in antioxidant substances, such as polyphenols, polysaccharides, peptides, etc., thus having antioxidant activity. Huangjiu brewing is different from beer and wine, and adopts an open fermentation process. The fermentation system is rich in amino acid content, complex in microbial species and more in microbial number, and complicated in bacterial community structure. The bacteria involved in the fermentation mainly include acetic acid bacteria, lactic acid bacteria, *Bacillus, Saccharopolyspora*, etc. However, the metabolites of microorganisms can not only bring a unique flavor to the huangjiu, but also make the huangjiu contain some harmful substances, such as biogenic amines.

Biogenic amine is a nitrogen-containing organic basic small molecule compound formed by decarboxylation of amino acids, which is commonly found in animals, plants and microorganisms. An appropriate amount of biogenic amine can promote growth, scavenge free radicals, improve metabolic activity, and enhance immunity. It has important physiological functions in the human body, but excessive intake of biogenic amines will cause the expansion of arteries, blood vessels and capillaries, resulting in adverse physiological reactions such as diarrhea, headache, abdominal cramps, and vomiting, and even lead to death. The biogenic amines are widely found in a variety of foods, the biogenic amines especially is rich in fermented foods such as yogurt, cheese, huangjiu, liquor, cooking wine, soy sauce, vinegar and wine.

The biogenic amines in fermented foods are mainly formed by the action of amino acid decarboxylase produced by microbial metabolism on free amino acids. In a fermentation process, microorganisms metabolize to produce protease and carboxypeptidase that act on the proteins in grains, and decompose to produce low-molecular-weight peptides and amino acids, thus providing abundant precursors for the production of the biogenic amines. In the case of the amino acid decarboxylase, a large number of biogenic amines will be generated.

At present, there is no report on the application of *Saccharopolyspora* in food fermentation and biogenic amine reduction in domestic and foreign research. Therefore, it is of a great significance to use modern biotechnology to screen microorganisms with excellent performance for the production of high-quality, high-yield and high-grade fermented foods with unique flavors as well as the improvement of fermented food safety.

SUMMARY

The objects of the present disclosure are to solve the problem of higher biogenic amine content in the existing traditional brewed foods, and to provide a strain of *Saccharopolyspora jiangxiensis* J3 with excellent performance, which can be used in a fermentation process of wine (huangjiu and cooking wine), fish and vinegar for biological enhancement, so as to reduce the biogenic amine content in fermented foods, improve the taste and flavor of the foods, and better exert the application of actinomycetes in the traditional fermented foods.

It is the first object of the present disclosure to provide a strain of *S. jiangxiensis* J3, and the *S. jiangxiensis* J3 has been preserved in China Center for Type Culture Collection (CCTCC) on Apr. 30, 2020 at Wuhan University, Wuhan, China, with a preservation number of CCTCC NO: M 2020104.

The *Saccharopolyspora* of the present disclosure has the following excellent properties:

(1) it is applied to a food fermentation system and will not affect the normal fermentation of food;

(2) the pure wheat koji produced by the strain is suitable for the fermentation of huangjiu, which can not only promote the rate of alcohol production but also increase the content of amino acids in the huangjiu;

(3) the amount of biogenic amines produced is less than 2.5 mg/L, so that the amount of the biogenic amines detected is very small;

(4) it can degrade tyramine, histamine, putrescine, and cadaverine; and (5) it can be applied to stinky mandarin fish fermentation, cooking wine fermentation and vinegar fermentation, and has the ability to reduce the biogenic amines.

It is the second object of the present disclosure to provide a microbial inoculum containing *S. jiangxiensis* J3.

In one implementation, the quantity of *S. jiangxiensis* J3 in each gram or milliliter of a starter is greater than or equal to $1\times10^6$ CFU.

In one implementation, the microbial preparation contains live cells of the *S. jiangxiensis* J3, dried bacterial cells obtained by freeze-drying, immobilized cells, liquid inocula, solid inocula, or strains in any other form.

It is the third object of the present disclosure to provide a compound microbial inoculum containing *S. jiangxiensis* J3.

In one implementation, the total quantity of *S. jiangxiensis* J3 in each gram or milliliter of a starter is greater than or equal to $1\times10^6$ CFU.

It is the fourth object of the present disclosure to provide pure wheat koji prepared by using strain of *S. jiangxiensis* J3.

In one implementation, a preparation method of the wheat koji is as follows: adding clear water into crushed wheat for wetting, then cooking the material subjected to wetting for sterilizing, inoculating the *S. jiangxiensis* J3 for fermentation to prepare the wheat koji.

In one implementation, the preparation method of the wheat koji includes the following steps:

(1) milling: breaking wheat grain tissues until the crushing degree of wheat is 3-5 pieces per grain, with a small amount of powder, and exposing starch;

(2) wetting: adding clear water in an amount of 30-45% of the mass of the material treated in step (1) into the material, and stirring for 15-25 min to make the material fully and evenly absorb water;

(3) cooking for sterilization: cooking the material treated in step (2) for sterilization;

(4) inoculating: after the material in step (3) is cooled to 40° C. or below, inoculating an activated strain, where the inoculation amount is $10^5$-$10^7$ CFU/mL; and (5) fermenting.

In one implementation, the fermentation in step (5) includes the following steps:

a) spore germination period: after a koji material is fed into a plate for 6 hours, slowly rising the product temperature to about 34-35° C., using an automatic control mode to start small air volume for indirect ventilation for 5-10 minutes at an interval of 2 hours to reduce the product temperature to 32° C., and requiring uniform blowing through;

b) mycelium growth period: making the mycelium begin to grow after 3-5 times of intermittent ventilation, rising the product temperature to 35° C. or above, continuously ventilating while the koji material begins to agglomerate, and maintaining the product temperature to be 35±2° C.;

c) mycelium propagation period: turning the koji material according to the first agglomeration when the product temperature rises rapidly at the time of 12 hours after inoculation, where before the koji material is turned, a temperature measuring probe should be raised first, a koji bending machine is turned on, the koji material is then spread, the temperature measuring probe is put down, and a ventilation and spray system is turned on;

d) after turning the koji material for the first time, maintaining the product temperature to be within a range of 36-37° C., and keeping ventilation and spraying smooth; and after about 20 hours, controlling the temperature to be 37° C. or below and turning the koji material for the second time when the koji material agglomerates again and turns white, and then controlling the product temperature to be within a range of 35±2° C.

It is the fifth object of the present disclosure to provide a method for preparing pure wheat koji by using strain of *S. jiangxiensis* J3, and application thereof in food fermentation or preparation of cigarettes and feeds.

In one implementation, the application refers to use in the field of fermented foods.

In one implementation, the application is for the preparation of fermented foods, drinks or condiments.

In one implementation, the foods include but are not limited to fermented or semi-fermented foods of fishes.

In one implementation, the drinks include but are not limited to huangjiu or cooking wine.

In one implementation, the condiments include but are not limited to vinegar.

In one implementation, according to the application, the pure wheat koji prepared by using the strain is mixed with brewing materials for fermentation. The fermented foods include but are not limited to huangjiu, cooking wine, vinegar, fish, cheese, etc.

In one implementation, in accordance with the method, the pure wheat koji is evenly mixed with raw materials such as rice and seeding yeast in a fermentor according to an inoculation amount of 10-16% for carrying out fermentation, and a traditional fermentation process is adopted during fermentation.

In one implementation, the fermentation process of huangjiu is as follows:

a) activated culture of yeast: inoculating yeast in a YPD medium, and performing activated culture at 30° C. for 24 h under the condition of 150 r/min;

b) production of seeding yeast: taking 600 g of steamed rice, and adding 1600 mL of clear water, 60 g of raw wheat koji, and 800 U/g of saccharifying enzyme for rice into the steamed rice, and carrying out saccharification at 55-65° C. for 3-4 hours; and when the apparent sugar content is not lower than 12° Bx after saccharification, sterilizing at 115° C. for 15 min, cooling down to 24-31° C. after sterilization, inoculating the mature yeast culture solution cultured in step a) according to an inoculation amount of 5%, and culturing at the temperature not exceeding 30° C. for 18-24 h under the condition of 150 r/min until maturity to obtain the seeding yeast.

c) carrying out blanking and fermentation according to a raw material ratio of the traditional huangjiu fermentation, where the addition amount of wheat koji is 40-50 g/L; in the first four days which are considered as a pre-fermentation stage, controlling the temperature to be within a range of 28-30° C., and carrying out fermentation for 4 days, where raking shall be performed at least once a day in the first 4 days, and the first raking time shall be 8-10 h; and in a post-fermentation stage, raking and stirring once a day at the temperature of 13-15° C., and continuously fermenting for 10-15 days.

In one implementation, a preparation method of cooking wine is as follows: using *S. jiangxiensis* for the fermentation of huangjiu, adding 5-15% by mass of salt into the huangjiu obtained by fermentation, sterilizing at 85-100° C., and hot filling.

In one implementation, a preparation method of vinegar is as follows: mixing bran, wheat bran and huangjiu thoroughly in a mass ratio of 1:4:10, inoculating 5% of vinegar fermented grains, turning the fermented grains from the material surface every day within the first 2 days after inoculation, and keeping the temperature at 35-42° C.; turning to the bottom of the material after 6-8 days; turning the fermented grains from the bottom every day from the $8^{th}$ to the $12^{th}$ day, and making the temperature naturally drop; and separating from the vinegar fermented grains to obtain raw vinegar, sterilizing at 85° C. for 30 min, and then ageing for 12 months.

In one implementation, liquor is fermented in two rounds. The first round of fermentation: after sorghum is steamed, cooling and inoculating the sorghum with *Aspergillus oryzae* seed liquid, and then culturing at 25-28° C. for 20-24 h; adding rice husk, Daqu, wheat bran, pure wheat koji containing *S. jiangxiensis*, and *S. cerevisiae* seed liquid, carrying out sealed fermentation for at least 30 days, and then steaming with wine; and the second round of fermentation: adding medium temperature Daqu into the raw materials obtained after the step of steaming with wine, inoculating the *S. cerevisiae* seed liquid with a concentration of $10^{10}$-$10^{12}$ CFU/mL, continuing to ferment for 12-15 days, and then steaming with wine.

In one implementation, a preparation method of fermented stinky mandarin fish includes the following steps:

(1) sample pretreatment: removing the viscera of mandarin fish, and weighing 3 kg of the treated mandarin fish;

(2) preparation of fermentation liquid: taking the mandarin fish and drinking water, calculated as 100%, where the mass of the mandarin fish is equal to that of the drinking water, adding 6% of salt, 1% of green Chinese onion, 0.6% of ginger, 0.1% of anise, 0.05% of fennel, 0.05% of cumin, 0.01% of pepper, 0.01% of Chinese prickly ash, and 300000 U neutral protease, and mixing evenly to obtain the fermentation liquid;

(3) inoculation: inoculating the fermentation liquid obtained in step (2) with the activated *S. jiangxiensis* J3 strain according to an inoculation amount of 10%, where the concentration of bacterium is $10^7$ CFU/mL; and (4) fermentation: soaking the mandarin fish in the fermentation liquid obtained in step (3), compacting the top layer with stones, and fermenting at 20° C. for 6 days to obtain the stinky mandarin fish.

In one implementation, cheese is prepared by adding *S. jiangxiensis* or a starter into sterilized milk, acidifying and then adding chymosin, obtaining a cheese clot after curding, and spraying the *S. jiangxiensis* onto the surface of the cheese clot for maturation.

In one implementation, cigarettes are prepared by spraying *S. jiangxiensis* J3 or a starter onto surfaces of tobacco leaves, and then fermenting the tobacco leaves at the temperature of 30-37° C. and the humidity of 70-80%.

In one implementation, feed is prepared by inoculating a mixture containing rice bran, straw and/or soybean meal with *S. jiangxiensis* J3 or a starter for fermentation.

It is the sixth object of the present disclosure to provide application of *S. jiangxiensis* J3 in reducing biogenic amines in fish fermentation as well as brewing of huangjiu, cooking wine, vinegar, cheese and cigarettes.

In one implementation, the biogenic amines include, but are not limited to, tyramine, histamine, putrescine, or cadaverine.

In one implementation, the brewed huangjiu, cooking wine and vinegar are first made into pure koji by using *Saccharopolyspora*, and the pure koji is then added during the fermentation of wine and vinegar.

The present disclosure has the beneficial effects that:

(1) The strain of the present disclosure is applied to a food fermentation system and will not affect the normal fermentation of food.

(2) The pure wheat koji produced by using the strain can be used for huangjiu fermentation, which can not only promote the alcohol yield, but also increase the amino acid content in huangjiu; *S. jiangxiensis* J3-containing pure-bred fermented huangjiu has no significant difference in amino acid content compared with a control group, and the content of amino acids in the huangjiu fermented by adding a compound microbial inoculum is the highest; the addition of the strain has no obvious effect on the flavor of the traditional huangjiu; and compared with the control group, the biogenic amine content in a sample group added with the *S. jiangxiensis* J3 decreases by 35.09%, which improves the amino acid content and nutritional value in the huangjiu, and achieves the purposes of increasing the contents of amino acids and volatile substances in the huangjiu and improving the quality of the huangjiu.

(3) The amount of biogenic amines produced by the *S. jiangxiensis* J3 is less than 2.5 mg/L, so that the amount of the biogenic amines detected is very small, and the biogenic amines are basically not produced. The degradation rates of the *S. jiangxiensis* J3 to tyramine, histamine, putrescine, cadaverine and total biogenic amines reach 81.55%, 100%, 51.8%, 40.01% and 69.09%, respectively, thus indicating that the strain has a good ability to reduce the biogenic amines.

(4) The *S. jiangxiensis* J3 has an effect of reducing the biogenic amines, which is applied to huangjiu fermentation. The content of the biogenic amines in fermented huangjiu added with the *S. jiangxiensis* J3 is 16.88±1.41 mg/L, which is reduced by 36.90% compared with a control group; the content of the biogenic amines in stinky mandarin fish added with the *S. jiangxiensis* J3 is reduced by 23.24% compared with a control group; the content of the biogenic amines in cooking wine added with the *S. jiangxiensis* J3 is reduced by 18.91%, compared with a control group; the content of the biogenic amines in vinegar added with the *S. jiangxiensis* J3 is reduced by 27.61% compared with a control group; and the content of the biogenic amines in cheese added with the *S. jiangxiensis* J3 is reduced by 13.33% compared with a control group.

(5) Compound microbial inoculum containing *Saccharopolyspora* has an effect of reducing the biogenic amines, which is applied to huangjiu fermentation. The content of the biogenic amines in fermented huangjiu added with the compound microbial inoculum Mix is 15.57±0.44 mg/L, which is reduced by 41.79% compared with a control group.

(6) The *S. jiangxiensis* J3 has effects of improving quality and reducing harm, which is applied to cigarette fermentation. The contents of harmful components such as tar, HCN, phenol, NH3 and nitrite in fermented tobacco leaves added with *S. jiangxiensis* J3 are decreased by 32.65%, 17.55%, 17.69%, 25.36% and 29.17%, respectively, compared with a control group.

(7) The *S. jiangxiensis* J3 has an effect of improving nutrient conversion rate, which is applied to feed fermentation. The contents of organic acids, amino acids and crude proteins in fermented feed added with the *S. jiangxiensis* J3 are increased by 37.26%, 18.57% and 23.41%, respectively, compared with a control group.

Biological Material Preservation

*S. jiangxiensis* J3, classified as *S. jiangxiensis* J3, has been preserved in China Center for Type Culture Collection (CCTCC) on Apr. 30, 2020 at Wuhan University, Wuhan, China, with a preservation number of CCTCC NO: M 2020104.

*Saccharopolyspora hirsuta* J2, classified as *S. hirsuta* J2, has been preserved in China Center for Type Culture Collection (CCTCC) on Apr. 30, 2020 at Wuhan University, Wuhan, China, with a preservation number of CCTCC NO: M 2020103.

DETAILED DESCRIPTION

Figure 1:
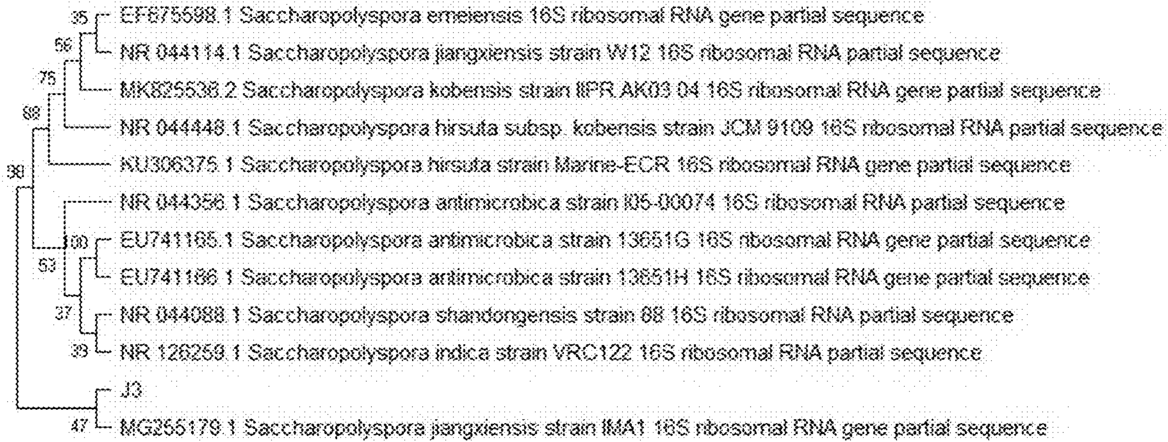
FIG. 1 shows a phylogenetic tree of *S. jiangxiensis* J3.
Figure 2A:
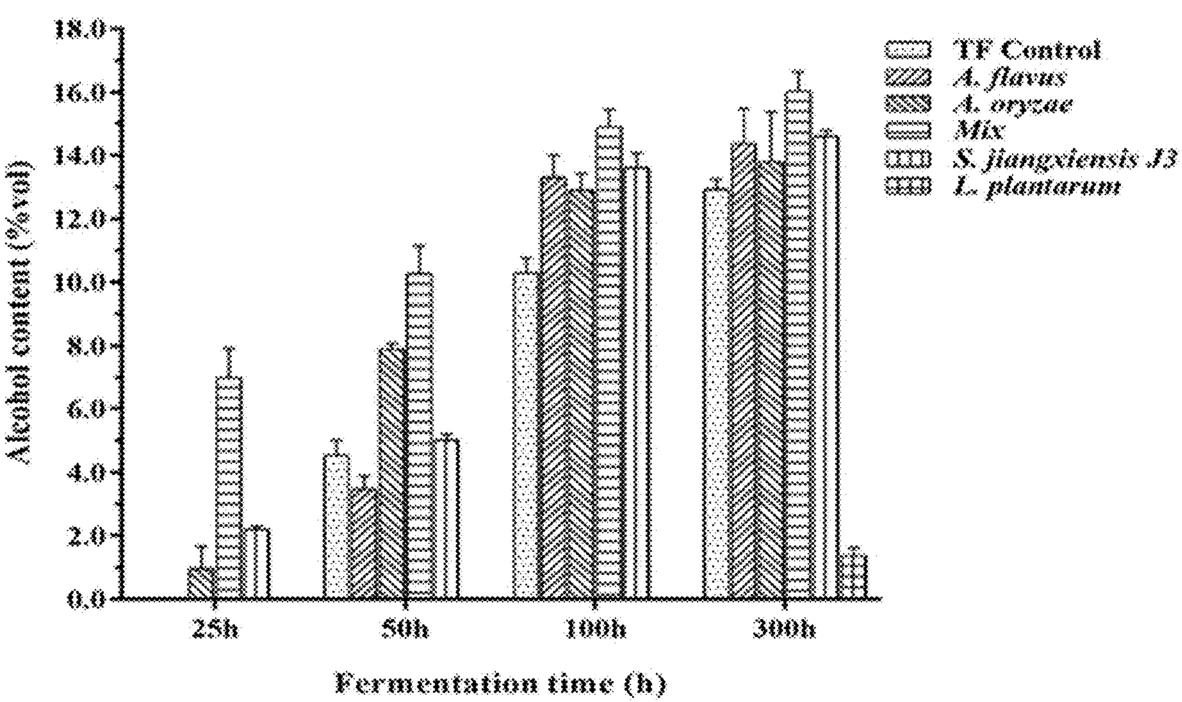
FIG. 2A shows changes of alcohol content in a huangjiu fermentation process.
Figure 2B:
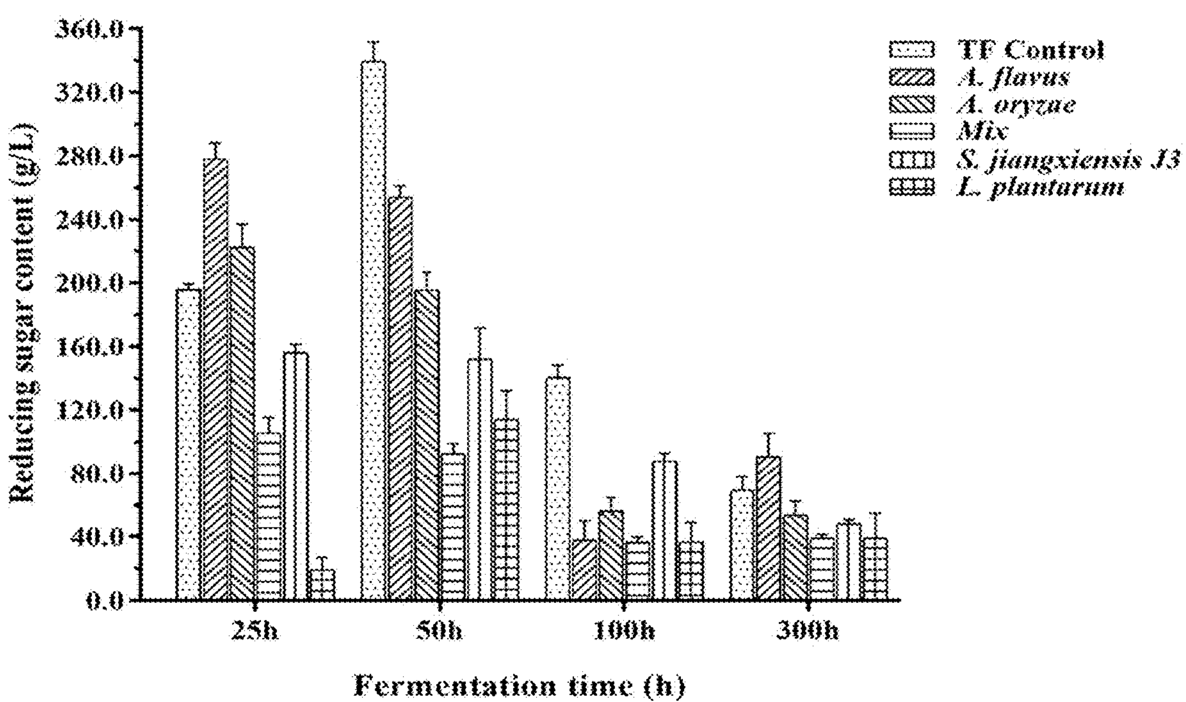
FIG. 2B shows changes of reducing sugar in a huangjiu fermentation process.
Figure 2C:
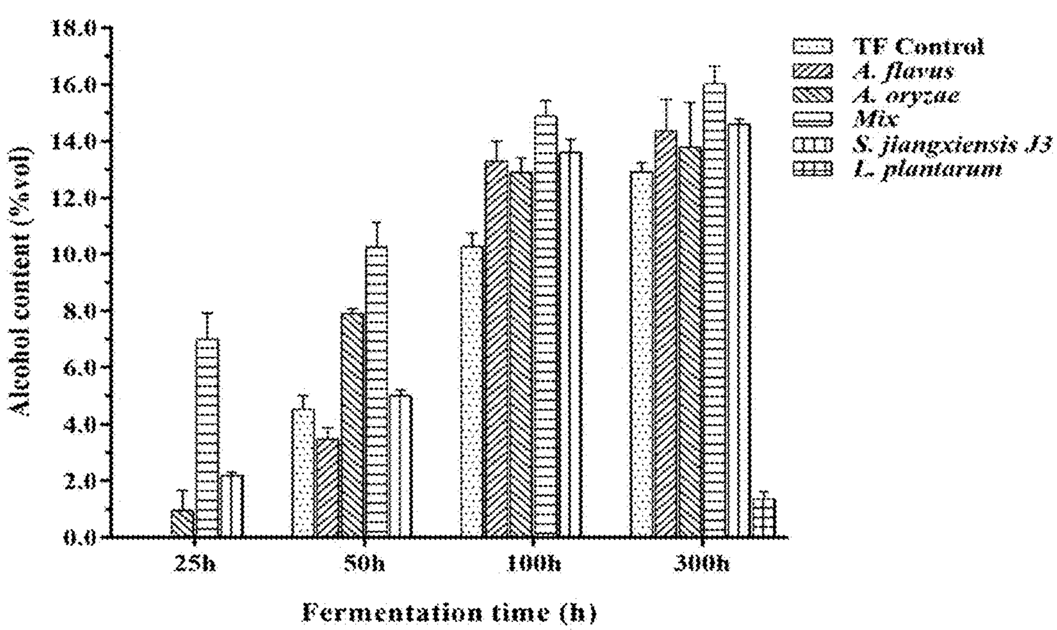
FIG. 2C shows changes of titratable acid in a huangjiu fermentation process.
Figure 2D:
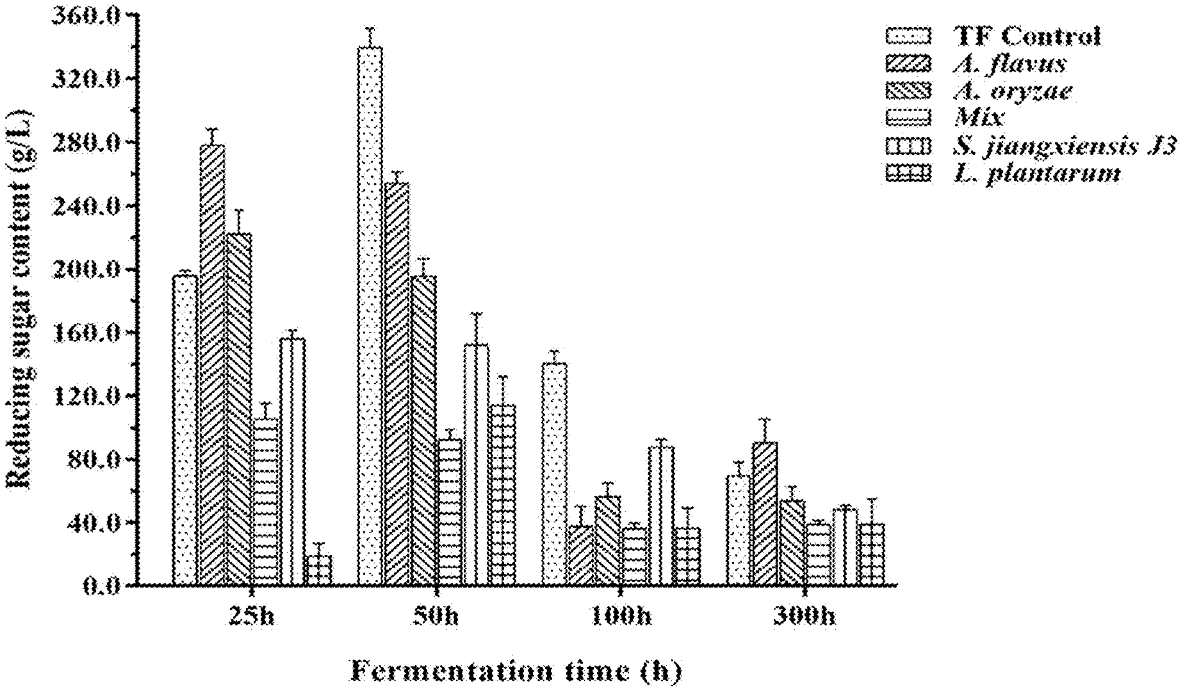
FIG. 2D shows changes of amino acid nitrogen in a huangjiu fermentation process.

Detection of physical and chemical indexes of huangjiu: alcohol content, amino acid nitrogen and total acid shall be determined according to GB/T 13662-2018. The content of biogenic amines and the flavor substances are detected by a high-performance liquid chromatography (HPLC) and a gas chromatography-mass spectrometry (GC-MS) instrument. The content of reducing sugar is determined by using a DNS method.

Example 1: Screening and Identification of *Saccharopolyspora*

(1) Sample Collection and Pretreatment

Wheat koji samples were collected from a huangjiu factory in Shaoxing City, Zhejiang Province, and the collected wheat koji was stored in a sealed sterile plastic bag at 4° C. Weighed 5 g of the wheat koji and put into a 50 mL centrifuge tube, add 30 mL of distilled water, placed in a shaker incubator at 30° C. and culture for 30 min.

(2) Plate Screening of Strains

Actinomycetes screening medium: 1.0 g/L of potassium nitrate, 0.5 g/L of potassium dihydrogen phosphate, 0.5 g/L of magnesium sulfate, 0.01 g/L of ferrous sulfate, 0.5 g/L of sodium chloride, 20.0 g/L of soluble starch, 15.0 g/L of agar, pH: 7.2-7.4 (25° C.).

In a sterile operating environment, a sterile pipette was used to suck 1 mL of a sample and the sample was placed in a 15 mL sterile centrifuge tube, sterile water was added to 10 mL and mixed well, and $10^{-1}$ sample homogenate was prepared. the sterile pipette was used to suck 1 mL of the $10^{-1}$ sample homogenate, and another 15 mL sterile was put into centrifuge tube, sterile water was added to 10 mL and mixed thoroughly, and $10^{-2}$ sample homogenate was prepared. According to the above operation, a series of $10^{-1}$-$10^{-6}$ tenfold increasing dilute homogenate of wheat koji, rice milk water and fermented mash were prepared accordingly.

100 μL of different dilutions of the homogenate of the wheat koji, the fermented mash and the rice milk water were separately absorbed, sample was applied to the actinomycetes screening medium and cultured for 1-7 days at 28° C. Single milky white, thin and slightly-wrinkled colonies having raised portions or convex surfaces on a plate with moderate in colony density were picked and inoculated on the actinomycetes screening medium by separately streaking, the colonies were repeatedly streaked to determine the pure colonies, and the selected strains were preserved.

(3) Strain Identification

The genome of the screened strains was extracted, and the screened strains were sequenced by means of 16S rDNA amplification.

PCR amplification primer 27F (5'-AGAGTTTGATCCTGGCTCAG-3') and 1492R (5'-GGTTACCTTGTTACGACTT-3').

PCR amplification system (50 μL): 25 μL of 2×Taq PCR Master Mix, 1 μL of an upper primer, 1 μL of a lower primer, and 1 μL of a template; and 22 μL of sterile water for supplementing was added to 50 μL.

PCR amplification procedures: pre-denaturation was carried out at 94° C. for 3 min, denaturation was carried out at 95° C. for 30 s, anneal was at 58° C. for 30 s, extension was at 72° C. for 2 min, where there were 35 cycles in total, and finally, extension was at 72° C. for 8 min.

The PCR products were detected by 1% agarose gel electrophoresis and sent to a gene sequencing company for sequencing. The 16S rDNA results of the PCR products were as shown in SEQ ID NO.1.

According to the returned sequencing results (shown in SEQ ID NO.1), BLAST sequence alignment was performed through NCBI official website, BLAST alignment is performed by using the obtained 16S rDNA sequence, and phylogenetic analysis is also carried out. The results, as shown in FIG. 1, indicate that the homologous similarity between the nucleotide sequence of a strain of J3 and *Saccharopolyspora S. jiangxiensis* (GenBank similar sequence number: MG255179.1) is 98.84% or above, and the strain is named as *S. jiangxiensis* J3.

(4) Analysis on Biogenic Amine Metabolism Ability of Strains

Strain activation: the preserved *S. jiangxiensis* J3 was inoculated into an actinomycetes liquid medium according to an inoculation amount of 10% and cultured on a shaker at 30° C. for 48 hours to obtain a first-level seed solution; and the activated strain was inoculated into the actinomycetes liquid medium according to an inoculation amount of 10% and cultured on the shaker at 30° C. for 48 hours at a rotation speed of 150 r/min.

Sample pretreatment: the strains was inoculated into a culture medium for detecting the production of biogenic amines and a culture medium for detecting the degradation of the biogenic amines, respectively, the strains were cultured on a shaker at 28° C. for 5 days and centrifuged for 5 min at 12000 r/min to collect supernatant.

Actinomycetes liquid medium: 1.0 g/L of potassium nitrate, 0.5 g/L of potassium dihydrogen phosphate, 0.5 g/L of magnesium sulfate, 0.01 g/L of ferrous sulfate, 0.5 g/L of sodium chloride, 20.0 g/L of soluble starch, pH: 7.2-7.4 (25° C.).

The culture medium for detecting the production of the biogenic amines: 0.4 g/L of L-tyrosine, 1 g/L of L-histidine, 1 g/L of L-lysine, 1 g/L of L-ornithine and 0.05 g/L of 5'-pyridoxal phosphate were added into the actinomycetes liquid medium.

The culture medium for detecting the degradation of the biogenic amines: 50 mg/L of biogenic amines (including histamine, tyramine, cadaverine, putrescine, spermine, spermidine, tryptamine, and β-phenethylamine) were added into the actinomycetes liquid medium, and the pH was adjusted to 6.0-6.2.

Determination method of biogenic amine content: 1 mL of a solution to be tested in a 15 mL centrifuge tube was accurately measured, 1 mL of a saturated $NaHCO_3$ solution was added and mixed well, 2 mL of a dansyl chloride (5 mg/mL of acetone) reagent was added and mixed well, and then the mixture was placed in a thermostat water bath at 65° C. for dark derivation for 30 min, and standing was carried out at room temperature, and then 0.5 mL of a saturated NaCl solution was added and mixed well, and then 5 mL of ether was added, vortex oscillation was carried out for 20 s, and standing was carried out for layering, then an upper organic phase was transferred into the 15 mL centrifuge tube, a lower aqueous phase was extracted once again, the two obtained extracts were merged, and then the product by blowing with nitrogen was dried in a water bath at 50° C.; 1 mL of acetonitrile was added, shook and mixed well, the residue was dissolved and filtered with a 0.22 μm filter membrane, and biogenic amine content was determined by means of high performance liquid chromatography (HPLC).

Analysis on the effect of reducing the biogenic amines by the *S. jiangxiensis* J3: the production amounts of various biogenic amines produced by the *S. jiangxiensis* J3 cultured in a medium with biogenic amine precursors are all less than 2.5 mg/L, so that the amount of the biogenic amines detected is very small, which indicates that the content of the biogenic amines is basically not detected, and thus it is considered that the biogenic amines are not produced. The degradation rates of tyramine, histamine, putrescine, cadaverine and total biogenic amines by the *S. jiangxiensis* J3 are 81.55%, 100%, 51.8%, 40.01% and 69.09% respectively. It showed that the strain has a good ability to reduce the biogenic amines.

Example 2: Activated Culture of a Strain of *S. jiangxiensis* J3

Actinomycetes liquid medium: 1.0 g/L of potassium nitrate, 0.5 g/L of potassium dihydrogen phosphate, 0.5 g/L of magnesium sulfate, 0.01 g/L of ferrous sulfate, 0.5 g/L of sodium chloride, 20.0 g/L of soluble starch, pH: 7.2-7.4 (measured at 25° C.).

PDA medium: 6.0 g/L of potato flour, 20.0 g/L of glucose, 20.0 g/L of agar, pH: 5.4-5.8, the PDA medium was autoclaved at 121° C. for 15 min; and a solid medium was added on this basis.

MRS medium: 10 g/L of beef extract, 10 g/L of peptone, 0.5 g/L of yeast extract, 20 g/L of glucose, 0.10 g/L of Tween 80, 5 g/L of sodium acetate, 2 g/L of dipotassium hydrogen phosphate, 2 g/L of diammonium hydrogen citrate, 0.58 g/L of magnesium sulfate, and 0.28 g/L of manganese sulfate.

*S. jiangxiensis* J3 screened in Example 1 was inoculated into the actinomycetes liquid medium according to an inoculation amount of 10%, and cultured on a shaker at 30° C. for 48 hours, so that a first-level seed solution was obtained. The activated strain was inoculated into the actinomycetes liquid medium according to an inoculation amount of 10-15%, and cultured on the shaker at 30° C. for 48 hours at a rotation speed of 150 r/min, so that bacterial liquid was obtained, and an order of magnitude of bacterial concentration thereof was $10^5$-$10^7$ CFU/mL; and after being cultured to be mature, the obtained bacterial liquid was used for the preparation of pure wheat koji.

Preserved *Aspergillus flavus* and *Aspergillus oryzae* were inoculated onto a PDA plate, and cultured at 28° C. for 3-5 days; then, the spore fluid was washed with sterile water, then transferred and inoculated into a PDA eggplant type flask again, and cultured at 28° C. for 3-5 days, so that bacterial liquid was obtained, and an order of magnitude of bacterial concentration thereof was $10^5$-$10^7$ CFU/mL; and after the spores were mature, it was used for the production of the pure wheat koji.

*Lactobacillus plantarum* was inoculated into the MRS medium according to an inoculation amount of 10%, and subjected to anaerobic culture at the constant temperature of 37° C. for 24 hours, so that a first-level seed solution was obtained. The activated seed solution was inoculated into the MRS medium again according to an inoculation amount of 10%, and subjected to anaerobic culture at the constant temperature of 37° C. for 24 hours, so that bacterial liquid was obtained, and an order of magnitudes of bacterial concentration thereof was $10^5$-$10^7$ CFU/mL; and after being cultured to be mature, the obtained strain was used for the production of the pure wheat koji.

Example 3: Preparation of *Saccharopolyspora* Pure Wheat Koji (1) Milling: wheat grain tissues were broke until the crushing degree of wheat was 3-5 pieces per grain, with a small amount of powder, and exposing starch;

(2) wetting: clear water in an amount of 35-45% of the mass of the material treated in step (1) was added into the material and stirred for 20-25 min to make the material fully and evenly absorb water;

(3) cooking for sterilization: the material treated in step (2) was sterilized at 121° C. for 30 min;

(4) inoculating: after the material in step (3) was cooled to 36° C., an activated strain was inoculated, where the concentration of bacterium during inoculation was $10^5$-$10^6$ CFU/mL, and the inoculation amount was 4‰-20%; and (5) after the koji material was fed into a plate, the appropriate product temperature and room temperature were kept, the koji material was stood and cultured for 6 hours, and then the koji material was treated according to the following steps:

a) spore germination period: after the koji material was fed into the plate for 6 hours, the product temperature slowly rose to about 34-35° C., an automatic control mode was used to start small air volume for indirect ventilation for 5-10 minutes at an interval of 2 hours to reduce the product temperature to 32° C., and there was a requirement for uniform blowing through;

b) mycelium growth period: the mycelium was made to begin to grow after 3-5 times of intermittent ventilation, the product temperature rose to 35° C. or above, ventilation was continuous while the koji material began to agglomerate, and the product temperature was maintained to be about 35° C.;

c) mycelium propagation period: the koji material was turned according to the first agglomeration when the product temperature rose rapidly at the time of 12 hours after inoculation, where before the koji material was turned, a temperature measuring probe should be raised first, a koji bending machine was turned on, the koji material was then spread, the temperature measuring probe was put down, and a ventilation and spray system was turned on;

d) after turning the koji material for the first time, the product temperature was maintained to be within a range of 36-37° C., and ventilation and spraying smooth were kept; and after about 20 hours, the temperature was controlled to be 37° C. or below, and the koji material was turned for the second time when the koji material agglomerated again and turns white, and then the product temperature was controlled to be about 35° C.;

(6) koji production: culturing for 75-100 h; and after the cultivation, the wheat koji was placed in a refrigerator at 4-7° C. for later use.

According to the above methods, pure wheat koji containing the *S. jiangxiensis* J3 and pure wheat koji containing *Saccharopolyspora hirsuta* J2 were prepared, respectively, and the orders of magnitudes of bacteria thereof were $10^{15}$ CFU/g.

Example 4: Application of *Saccharopolyspora* Wheat Koji in Huangjiu Fermentation (1) A Raw Material Ratio (Calculated by Fermentation Volume Per Liter) for the Traditional Huangjiu Fermentation Selected in this Example was as Follows:

steamed rice: 500 g; clear water 417L; seeding yeast: 38 g;

(2) Traditional Huangjiu Brewing Process a) Activation culture of yeast: yeast in a glycerin preservation tube was transferred and inoculated into a YPD medium on a sterile operating platform, and the yeast was cultured at 30° C. for 24 hours under the condition of 150 r/min; then sample was transferred and inoculated into the prepared seeding yeast, and the inoculated yeast was cultured at 30° C. for 18-24 hours under the condition of 150 r/min for later use;

b) preparation of seeding yeast: 600 g of the steamed rice was taken, 1600 mL of the clear water, 60 g of raw wheat koji, and 800 U/g of saccharifying enzyme for rice were added into the steamed rice, and saccharification was carried out at 55-65° C. for 3-4 hours; and when the apparent sugar content was not lower than 12° Bx after saccharification, sterilization was at 115° C. for 15 min, cooling down to 24-31° C. after sterilization, 5% mature yeast seed culture solution was inoculated and cultured at the temperature not exceeding 30° C. for 24 h until maturity to obtain the seeding yeast; and c) blanking and fermentation was carried out according to the raw material ratio of the traditional huangjiu fermentation described in step (1).

Experimental group: pure wheat koji: 45.3 g, an order of magnitudes of *saccharopolyspora* thereof was $1\times10^{15}$ CFU/g; control group: raw wheat koji: 39.3 g; cooked wheat koji: 6.0 g.

In the first four days which were considered as a pre-fermentation stage, the temperature was controlled to be within a range of 28-30° C., and fermentation was carried out for 4 days, where raking shall be performed at least once a day in the first 4 days, and the first raking time shall be 8-10 h; and in a post-fermentation stage, the yeast was raked and stirred once a day at the temperature of 13-15° C., and fermentation was continuous for 10-15 days.

For the control group (TF Control), the pure wheat koji in (3) of this example was adjusted to 39.3 g/L of raw wheat koji and 6.0 g/L of cooked wheat koji which were sampled from a factory.

A compound microbial inoculum group (Mix) was added with pure wheat koji containing *Saccharopolyspora hirsuta* J2 and pure wheat koji containing the *S. jiangxiensis* J3 in a ratio of 1:1, with a total amount of 45.3 g.

Changes in physical and chemical Indexes during the fermentation of huangjiu: in order to further verify the role of *Saccharopolyspora* in the fermentation of huangjiu, changes (see FIG. 2A-FIG. 2D) in the physical and chemical indexes (such as alcohol content, reducing sugar, titratable acid and amino acid nitrogen) of the traditional wheat koji and pure wheat koji during the fermentation are compared. There are 5 wheat koji fermentation group in total, which are *A. flavus* (bacterium commonly used in huangjiu fermentation), *A. oryzae* (bacterium commonly used in Japanese sake brewing), Mix (*S. jiangxiensis* J3 and *Saccharopolyspora hirsuta* J2 mixed wheat koji fermentation group), *S. jiangxiensis* J3 and *L. plantarum*, respectively. These 5 kinds of pure wheat koji are respectively fermented together with *S. cerevisiae* by using the traditional brewing method according to a) to c) in step 2 of this Example. By the end of the fermentation, except for the *L. plantarum* group, the alcohol contents, acidities and amino acid nitrogen contents of the other groups all reach the national standards for huangjiu. The titratable acid content of the *L. plantarum* group increases rapidly to 17.50 g/L, and the sample shows obvious rancidity.

Amino acid content in fermented huangjiu samples: an HPLC method is used to analyze the amino acid content in fermented huangjiu. The amino acid contents of Mix, *A. flavus* and *A. oryzae* experimental groups are not much different, but they are all significantly higher than that of the control group (TF Control); and the total amino acid content of the experimental group added with *S. jiangxiensis* J3 is not much different from that of the control group, and the contents of some amino acids thereof are significantly higher than those of the control group.

TABLE 1

Analysis on amino acid contents in fermented huangjiu samples

| mg/L | TF Control | *A. flavus* | *A. oryzae* | *S. jiangxiensis* J3 | *L. plantarum* |
|---|---|---|---|---|---|
| Asp | 172.94 ± 15.89 | 255 ± 14.24 | 333.26 ± 7.48 | 199.4 ± 28.17 | 99.89 ± 7.78 |
| Glu | 516.86 ± 42.94 | 783.95 ± 12.37 | 866.45 ± 27.67 | 498.28 ± 71.53 | 415.12 ± 32.04 |
| Asn | 123.95 ± 7.52 | 153.64 ± 30.65 | 184.51 ± 3.41 | 111.75 ± 23.6 | 95.89 ± 8.05 |
| Ser | 67.66 ± 3.83 | 90.51 ± 18.2 | 274.78 ± 5.61 | 101.12 ± 12.5 | 27.02 ± 7.15 |
| Gln | 315.06 ± 17.31 | 433.09 ± 15.19 | 438.03 ± 7.36 | 299.04 ± 46.13 | 115.66 ± 47.26 |
| His | 80.01 ± 8.57 | 105.37 ± 10.58 | 121.28 ± 5.8 | 62.81 ± 17.83 | 50.65 ± 18.85 |
| Gly | 169.7 ± 19.75 | 292.95 ± 5.67 | 374.39 ± 18.53 | 240.61 ± 20.66 | 80.2 ± 10.89 |
| Thr | 101.18 ± 20.49 | 151.8 ± 6.19 | 131.38 ± 11.09 | 55.69 ± 7.81 | 44.36 ± 4.78 |
| Arg | 313.12 ± 213.87 | 524.16 ± 184.11 | 412.13 ± 5.66 | 384.33 ± 80.6 | 713.42 ± 74.24 |
| Aala | 327.06 ± 33.76 | 431.84 ± 22.42 | 553.68 ± 3.08 | 423.41 ± 47.88 | 154.45 ± 7.95 |
| gaga | 86.89 ± 13.71 | 101.5 ± 3.53 | 117.58 ± 2.45 | 151.08 ± 62.91 | 106.25 ± 15.86 |
| tyr | 346.68 ± 30.96 | 334.19 ± 45.55 | 490.71 ± 6 | 297.97 ± 40.1 | 250.97 ± 13.44 |
| cys-s | 65.91 ± 2.07 | 101.36 ± 44.88 | 9.74 ± 1.71 | 28.92 ± 14.23 | 25.28 ± 21.25 |
| val | 241.78 ± 9.77 | 334.94 ± 3.44 | 325.35 ± 2.51 | 245.62 ± 33.19 | 143.27 ± 10.84 |
| met | 67.06 ± 0.63 | 102.32 ± 2.82 | 77.07 ± 1.76 | 23.53 ± 2.76 | 41.15 ± 1.46 |
| trp | 101.26 ± 5.8 | 135.6 ± 5.44 | 139.43 ± 1.15 | 111.35 ± 25.44 | 83.05 ± 4.56 |
| phe | 374.52 ± 10.99 | 495.37 ± 3.34 | 451.88 ± 2.66 | 279.74 ± 37.17 | 277.99 ± 10.76 |
| ile | 179.49 ± 9.85 | 261.47 ± 10 | 290.16 ± 5.36 | 149.25 ± 16.88 | 100.74 ± 7.66 |
| leu | 597.15 ± 12.93 | 836.29 ± 13.54 | 703.73 ± 6.12 | 377.94 ± 42.1 | 339.71 ± 20.96 |

TABLE 1-continued

| Analysis on amino acid contents in fermented huangjiu samples | | | | | |
|---|---|---|---|---|---|
| mg/L | TF Control | *A. flavus* | *A. oryzae* | *S. jiangxiensis* J3 | *L. plantarum* |
| lys | 302.76 ± 17.5 | 338.29 ± 16.8 | 275.44 ± 0.53 | 208.68 ± 44.52 | 181.68 ± 26.3 |
| pro | 33.26 ± 20.14 | 43.72 ± 6.69 | 59 ± 9.81 | 115.82 ± 27.26 | 128.42 ± 30.41 |
| Total | 4584.28 ± 105.28 | 6307.36 ± 322.13 | 6630 ± 101.19 | 4366.34 ± 567.73 | 3475.15 ± 227.53 |

Note:
gaga is γ-aminobutyric acid.

(3) Analysis on the Effect of Reducing Biogenic Amines by *Saccharopolyspora*

Analysis of the biogenic amine-reducing effect of *S. jiangxiensis* J3 and compound microbial inoculum (Mix group): the content of biogenic amines in the fermented huangjiu is detected by HPLC, indicating that compared with the control group, the content of the biogenic amines in the sample group added with the *S. jiangxiensis* J3 is decreased by 35.09%, the content of the biogenic amines in the sample group added with *Saccharopolyspora hirsuta* J3 is decreased by 21.71%, and the content of the biogenic amines in the compound microbial inoculum (Mix group) added with *Saccharopolyspora hirsuta* J2 and the *S. jiangxiensis* J3 is decreased by 42.17%.

(4) Flavor Analysis of Pure-Bred Fermentation and Traditional Fermentation

Figure 3:
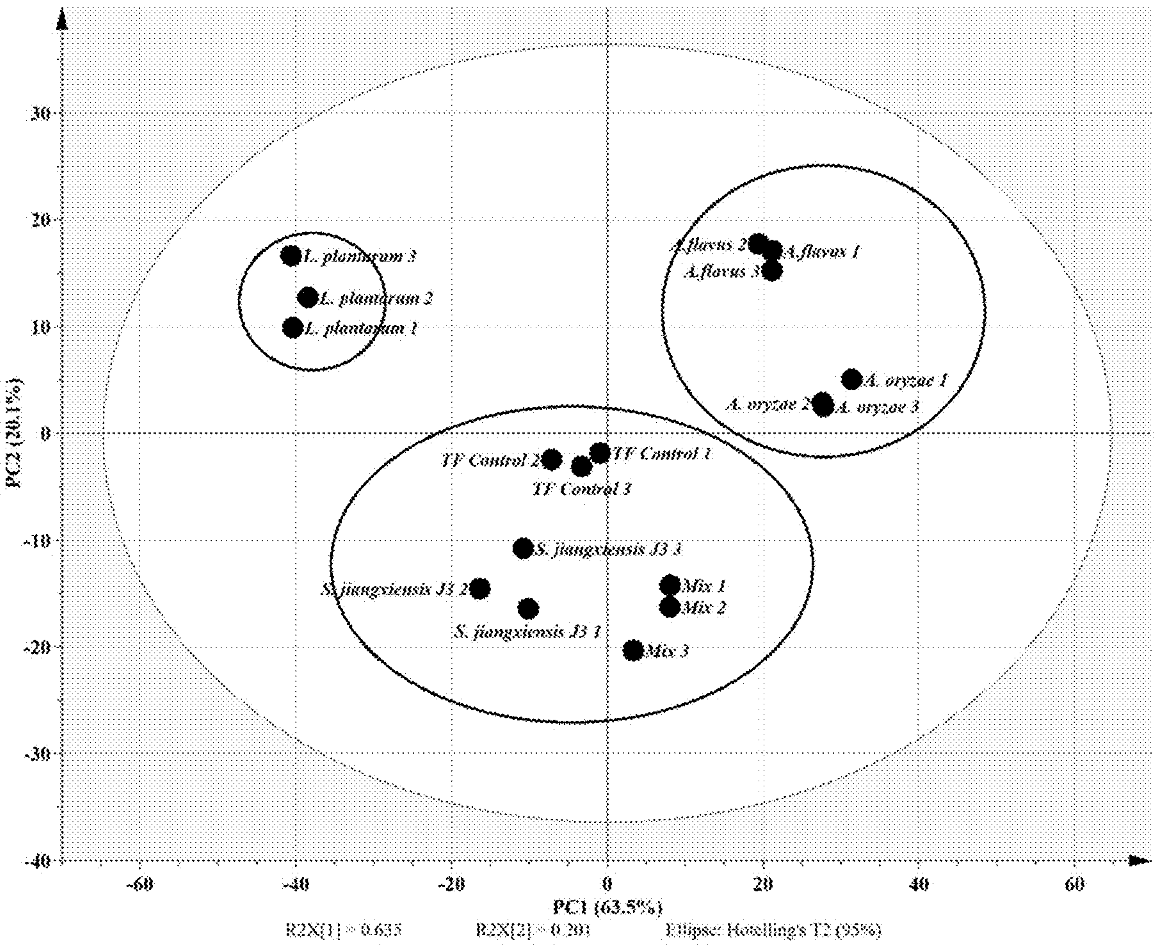
FIG. 3 shows principal component analysis of flavor substances in a fermented huangjiu sample.

Variation and similarity of flavor components in pure-bred and conventionally fermented samples are analyzed by using principal component analysis. Biplot analysis of all the samples shows that the cumulative contribution rate of variance of the first two principal components is 83.6%, which can explain the flavor differences in most of the fermented samples. As can be seen from FIG. 3, the traditional fermentation group is clustered with the Mix group and the *S. jiangxiensis* J3 group, and is clearly separated from the *Aspergillus* (*A. flavus* and *A. oryzae*) group and the *L. plantarum* group, which indicates that *Saccharopolyspora* is involved in the synthesis of most flavor substances and plays a leading role in the fermentation of huangjiu.

Embodiment 5: Application of *Saccharopolyspora* Inoculum in Huangjiu Fermentation The traditional huangjiu blanking formula in Example 4 was used for huangjiu fermentation. A Mix group and an *S. jiangxiensis* J3 group are separately set up in the experimental group. The difference is that the wheat koji inoculation ratios of the two groups are both 10%; the *S. jiangxiensis* J3 group is inoculated with pure wheat koji containing *S. jiangxiensis* J3; and the Mix group is inoculated with compound microbial inoculum wheat koji which applies mixed bacteria liquid of *S. jiangxiensis* J3 and *Saccharopolyspora hirsuta* J2 and is prepared according to a method of Example 3. The huangjiu brewing process and index determination method are carried out with reference to Example 4.

(1) Influence on Basic Physical and Chemical Indexes of Huangjiu

According to Table 2, it can be seen that the alcohol content of each group reaches about 14% v/v after fermentation, and the reducing sugar, total acid and amino acid nitrogen contents of all samples are 4.52-5.03 g/L, which all meet the physical and chemical requirements for huangjiu. Significance analysis shows that the alcohol content, total acid content and amino acid nitrogen content of the Mix group and the *S. jiangxiensis* J3 group are not significantly different from those of the control group (P>0.05), indicating that the inoculation of *S. jiangxiensis* J3 has little effect on the important physical and chemical indexes of the huangjiu during fermentation and will not adversely affect the fermentation process of the huangjiu.

TABLE 2

| Physical and chemical indexes of huangjiu at end of fermentation | | | |
|---|---|---|---|
| Index | Control group | Mix group | *S. jiangxiensis* J3 group |
| Alcohol content (% v/v; 20° C.) | 14.20 ± 0.60 | 14.20 ± 0.72 | 14.30 ± 0.50 |
| Reducing sugar content (g/L) | 20.02 ± 1.64 | 24.25 ± 0.23 | 9.45 ± 3.13 |
| Total acid content (g/L) | 4.68 ± 0.09 | 4.74 ± 0.26 | 4.81 ± 0.16 |
| Amino acid nitrogen content (g/L) | 0.82 ± 0.04 | 0.84 ± 0.06 | 0.82 ± 0.02 |

(2) Influence of *Saccharopolyspora* on Content of Biogenic Amines in Huangjiu

After the fermentation, the biogenic amine contents of samples inoculated with a compound microbial inoculum Mix group and an *S. jiangxiensis* J3 group are 15.57±0.44 mg/L and 16.88±1.41 mg/L respectively, which are both lower than 26.75±2.39 mg/L of the control group. compared with the control group, the *S. jiangxiensis* J3 group is decreased by 36.90%. It indicates that compound microbial inoculum Mix and *S. jiangxiensis* J3 have the effect of reducing the content of biogenic amines.

In summary, the inoculation of the compound microbial inoculum Mix and the *S. jiangxiensis* J3 in a huangjiu fermentation system does not affect the normal quality of huangjiu, and the total amine degradation rates of the compound microbial inoculum Mix and the *S. jiangxiensis* J3 reach 41.79% and 36.90% of the control group, respectively. The result indicates that the direct addition of the compound microbial inoculum Mix or the *S. jiangxiensis* J3 has the potential to be used in the production of the huangjiu and the regulation of the content of biogenic amines in the huangjiu. The compound microbial inoculum Mix has a better degradation effect on the biogenic amines in the huangjiu.

Example 6: Application of *S. Jiangxiensis* J3 in Reducing Content of Biogenic Amines in Fermented Fish Strain activation was performed by using the method in Example 1.

The specific process for the fermentation of stinky mandarin fish with neutral protease was as follows:

(1) sample pretreatment: the viscera of mandarin fish was removed, and 3 kg of the treated mandarin fish was weighed;

(2) preparation of fermentation liquid: the mandarin fish and drinking water were taken, calculated as 100%, where the mass of the mandarin fish was equal to that of the drinking water, 6% of salt, 1% of green Chinese onion, 0.6% of ginger, 0.1% of anise, 0.05% of fennel, 0.05% of cumin, 0.01% of pepper, 0.01% of Chinese prickly ash, and 300000 U neutral protease were added and mixed evenly to obtain the fermentation liquid;

(3) inoculation: the fermentation liquid was divided into two parts, one part was inoculated with the activated *S. jiangxiensis* J3 strain according to an inoculation amount of 10%, where the concentration of bacterium is $10^7$ CFU/mL, and the other part was not inoculated with the activated *S. jiangxiensis* J3 strain; and (4) fermentation: the mandarin fish in the fermentation liquid obtained after inoculation in step (3) was soaked, the top layer was compacted with stones, and fermentation was at 20° C. for 6 days to obtain the stinky mandarin fish.

Determination method of biogenic amines: 5.0 g of a minced fish sample was weighed and put into a 50 mL centrifuge tube, 20 mL of 5% trichloroacetic acid was added, and ultrasonic treatment was carried out for 30 min, the product was transferred into a 50 mL stoppered centrifuge tube and centrifuged for 10 min at 6000 r/min, the supernatant was transferred into a 50 mL volumetric flask, the residue was extracted with 20 mL of the above solution once again, the obtained supernatant was merged and diluted to the mark; then, 1 mL of the supernatant was accurately measured and put into the 15 mL centrifuge tube, 1 mL of a saturated $NaHCO_3$ solution was added and mixed well, 2 mL of a dansyl chloride (5 mg/mL acetone) reagent was added, mixed well, and placed in a thermostat water bath at 65° C. for dark derivation for 30 min; and standing was carried out at room temperature, and then 0.5 mL of a saturated NaCl solution was added and mixed well, and then 5 mL of ether was added, vortex oscillation was carried out for 20 s, standing was carried out for layering, then an upper organic phase was transferred into the 15 mL centrifuge tube, a lower aqueous phase was extracted once again, the two obtained extracts were merged, and then the product by blowing with nitrogen in a water bath was dried at 50° C.

1 mL of acetonitrile was added, shook and mixed well, the residue was dissolved and filtered with a 0.22 μm filter membrane, and biogenic amines were determined by means of high performance liquid chromatography (HPLC).

After fermentation, the biogenic amines in the stinky mandarin fish fortified with compound microbial inoculum Mix is decreased by 20.87% compared with a control group; and the biogenic amines in the stinky mandarin fish fortified with *S. jiangxiensis* J3 is decreased by 23.24% compared with a control group.

Example 7: Application of *S. Jiangxiensis* J3 in Reducing Content of Biogenic Amines in Cooking Wine The biogenic amine content was determined by using the method in Example 1.

The pure fermented huangjiu is obtained according to the brewing method in Example 4. 10% by mass of salt was added into the fermented huangjiu, and the obtained mixture was sterilized by a sterilizer at 85° C. and subjected to hot-filling for 30 min.

The effect of strains on reducing the biogenic amines in the cooking wine is analyzed: HPLC is used to detect the content of the biogenic amines in the cooking wine. Compared with a control group, the biogenic amine contents of the sample groups added with compound microbial inoculum Mix and *S. jiangxiensis* J3 are decreased by 23.16% and 18.91%, respectively.

Example 8: Application of *S. Jiangxiensis* J3 in Reducing Content of Biogenic Amines in Vinegar The pure fermented huangjiu obtained according to the brewing method in Example 4 was used as a raw material for acetic acid fermentation; and the biogenic amine content was determined by using the method in Example 1.

Acetic acid fermentation adopted a solid-state fermentation process: bran, wheat bran and huangjiu were mixed thoroughly in a mass ratio of 1:4:10, 5% of vinegar fermented grains were inoculated, the fermented grains from the material surface was turned every day within the first 2 days after inoculation, and the temperature was kept at 35-42° C.; the bottom of the material was turned over after 6-8 days; the fermented grains from the bottom was turned every day from the 8*th* to the 12*th* day, and the temperature was to made drop naturally; the vinegar fermented grains were separated to obtain raw vinegar, sterilization was at 85° C. for 30 min, and then aging was for 12 months; and the product was autoclaved and then hot filling was performing.

Analysis on the biogenic amine reducing effect of compound microbial inoculum Mix and *S. jiangxiensis* J3: the acetic acid content in the obtained solid-state fermentation brewed vinegar is 55 g/L. The contents of biogenic amines in samples are detected, and compared with a control group, the biogenic amine contents of the sample groups added with compound microbial inoculum Mix and *S. jiangxiensis* J3 are decreased by 25.08% and 27.61%, respectively.

Example 9: Application of *S. Jiangxiensis* J3 in Reducing Content of Biogenic Amines in Liquor

*Saccharopolyspora* pure wheat koji used in liquor brewing referred to the production method of wheat koji in Example 3. The biogenic amine content was determined by using the method in Example 1.

A two-round fermentation method was adopted for liquor brewing. The first round of fermentation: after sorghum was steamed, the sorghum was cooled to 25° C. by air-cooling, 4% *Aspergillus oryzae* seed liquid was added and cultured at 28° C. for 24 h; and 10% of rice husk, 15% of Daqu, 8% of wheat bran, and 5-9% of pure wheat koji prepared in Example 3, were added, *S. cerevisiae* seed liquid was inoculated according to a proportion of 1%, sealing and fermentation were for 30 days, and then wine was steamed. The second round of fermentation: 10% of medium temperature Daqu was added, the *S. cerevisiae* seed liquid was inoculated with a concentration of $10^{10}$-$10^{12}$ CFU/mL according to the proportion of 1%, fermentation was continuous for 12-15 days, and then wine was streamed.

Analysis on the biogenic amine reducing effect of *S. jiangxiensis* J3: the distilled liquor is blended to an alcohol content of 60% (V/V), the content of biogenic amines in a sample obtained after the blending is detected, and the biogenic amine content of the sample group added with *S. jiangxiensis* J3 is reduced.

Example 10: Application of *S. jiangxiensis* J3 in Reducing Content of Biogenic Amines in Soy Sauce The method in Example 1 was used to activate strains and determine biogenic amine content. Soy sauce was brewed with a high saline diluting method:

(1) firstly, soybean meal was mixed with wheat evenly in a ratio of 1:1, and then the obtained mixture was steamed;

(2) *S. jiangxiensis* J3 seed liquid was added according to a proportion of 5‰-10%, where the concentration of bacterium thereof was $10^5$-$10^6$ CFU/mL, and then saline water in an amount being about 1.5-2 times of the mass of materials was added, where the final salt content and water content of soy sauce mash were about 18% and 65%, respectively, and then mixed well;

(3) soy sauce fermentation: the initial fermentation temperature was controlled to be 14-16° C., where the temperature gradually rose to about 35° C. along with the fermentation progress and continued to ferment for about 5 months;

(4) after the fermentation, the soy sauce mash was pressed with a frame to remove bean sauce mash; after the pressing was completed, diatomite filtration and membrane filtration were carried out to remove precipitates; and the filtered and clarified soy sauce was pasteurized and filled.

Analysis on the biogenic amine reducing effect of *S. jiangxiensis* J3 shows that compared with a control group, the biogenic amine contents of soy sauce products added with *S. jiangxiensis* J3 are decreased.

Example 11: Preparation of Starter

Actinomycetes liquid medium: 1.0 g/L of potassium nitrate, 0.5 g/L of potassium dihydrogen phosphate, 0.5 g/L of magnesium sulfate, 0.01 g/L of ferrous sulfate, 0.5 g/L of sodium chloride, 20.0 g/L of soluble starch, pH: 7.2-7.4 (measured at 25° C.).

The *S. jiangxiensis* J3 screened in Example 1 was inoculated into the actinomycetes liquid medium according to an inoculation amount of 10%, and shake cultivation was carried out at 30° C. for 48 h, so that a cell culture solution was obtained. The cell culture solution was centrifuged to collect bacterial cells, and a cell protective agent was then added; and the cell protective agent includes but is not limited to glycerin, trehalose, skimmed milk powder, etc.

Example 12: Application of *S. Jiangxiensis* J3 in Reducing Content of Biogenic Amines in Cheese During Fermentation The method in Example 1 was used to activate strains and determine biogenic amine content. Fresh milk was homogenized and pasteurized, 0.1 mL/L of a mixed bacterial solution (with a concentration of $1\times10^8$-$10^9$ CFU/mL) of *Lactobacillus bulgaricus* and *Lactobacillus plantarum*, the ratio of which was 1:1, was added into the fresh milk that was cooled to the room temperature, the obtained mixture was stirred evenly and then subjected to acidification at 32-35° C. for 30 min, 0.05 g/L of chymosin was added and mixed well to form curd, and the formed curd was cut to remove whey, so that a cheese clot was obtained; and the surface of the cheese clot was sprayed with $10^5$-$10^6$ CFU/mL of *S. jiangxiensis* J3 and was cultured at 30-37° C. for 3-5 days until it grew and became mature, 3.0 g/L of salt was added, and the finished cheese was formed by pressing.

The determination of the fermented finished cheese shows that the biogenic amine content of the finished cheese added with *S. jiangxiensis* J3 is reduced by 13.33% compared with a control group.

Example 13: Application of *S. Jiangxiensis* J3 in Improving Quality and Reducing Harm of Cigarette Fermentation Strain activation was performed by using the method in Example 1. 10000 g of an activated bacterial solution was centrifuged at 4° C. for 15 min, and the collected bacteria were prepared into $10^5$-$10^6$ CFU/mL of an *S. jiangxiensis* J3 bacterial solution with sterile water. The bacterial solution was evenly sprayed onto the surfaces of tobacco leaves and fully mixed, and the obtained tobacco leaves were treated with the same amount of sterile water as a control; fermentation culture was carried out for 15 days in a constant temperature and humidity incubator with temperature of 30-37° C. and humidity of 70-80%, and ventilation was carried out every day; and after the culture, the tobacco leaves were dried until the moisture content was 15% or below.

The quality of the fermented tobacco leaves is determined. The aroma components of the fermented tobacco leaves are significantly increased, the impurity gases are reduced, and the irritation is weakened. Compared with a control group, the contents of harmful components such as tar, HCN, phenol, NH3 and nitrite in the fermented tobacco leaves are decreased by 32.65%, 17.55%, 17.69%, 25.36% and 29.17%, respectively.

Example 14: Application of *S. Jiangxiensis* J3 in Improving Nutrient Conversion Rate of Feed Fermentation Strain activation was performed by using the method in Example 1. Rice bran, straw and soybean meal were mixed evenly according to a ratio of (1-5):(1-5):2, and crushed to make a fermented product. Water was added according to a material to water ratio of 1:0.5-0.9*, S. jiangxiensis* J3 was inoculated according to a ratio of 10%0-10% and stirred evenly, where the concentration of bacterium thereof was $10^5$-$10^6$ CFU/mL, and natural fermentation was carried out at 30-40° C. for 4-9 days; and after fermentation, the product was dried until the water content was 15% or below, and biological fermented feed was thus obtained.

Analysis on the quality of the fermented feed: the obtained fermented feed has special aroma, is rich in nutrition and contains balanced amino acids. Compared with a control group, the organic acid content, amino acid content and crude protein content of the fermented feed are increased by 37.26%, 18.57% and 23.41%, respectively.

Although the present disclosure has been disclosed as above by exemplary embodiments, it is not intended to limit the present disclosure. Anyone familiar with this technology can make various changes and modifications without departing from the spirit and scope of the present disclosure. Therefore, the protection scope of the present disclosure shall be prevail as defined in the Claims.

What is claimed is:

1. A microbial preparation consisting of a freeze-dried formulation of *Saccharopolyspora jiangxiensis* J3 cells and skimmed milk powder, and wherein the freeze-dried formulated *S. jiangxiensis* J3 has been preserved in China Center for Type Culture Collection (CCTCC) with a preservation number of CCTCC NO: M 2020104.

2. The microbial preparation according to claim 1, wherein the quantity of the *S. jiangxiensis* J3 is greater than or equal to $1\times10^6$ CFU.

3. A method of preparing a wheat koji comprising adding the microbial preparation according to claim 1 to cooked wheat.

4. The method of preparing a wheat koji according to claim 3 further comprises:

i) cooking wheat that has been subjected to milling and wetting, ii) inoculating the cooked wheat with the microbial preparation of the *S. jiangxiensis* J3, wherein an inoculation amount is $10^5$ to $10^7$ CFU/mL, and iii) fermenting the cooked wheat and microbial preparation to obtain the wheat koji.

5. The method of preparing a wheat koji according to claim 4, wherein step i) further comprises:

(a) milling wheat grain by breaking wheat grain tissues and exposing starch to produce a material;

(b) fermenting the material of step (a) by adding water in an amount of 30% to 45% of the mass of the material treated into the material, and stirring for 15 to 25 minutes to obtain a treated material;

(c) cooking the treated material obtained in step (b) for sterilization to obtain a sterilized material; and (d) cooling the sterilized material from step (c) to 40° C. or below to obtain the cooked wheat.

* * * * *